(12) United States Patent
Adler

(10) Patent No.: US 8,110,799 B2
(45) Date of Patent: Feb. 7, 2012

(54) CONFOCAL SECONDARY ELECTRON IMAGING

(75) Inventor: David L. Adler, San Jose, CA (US)

(73) Assignee: KLA-Tencor Corporation, Milpitas, CA (US)

( * ) Notice: Subject to any disclaimer, the term of this patent is extended or adjusted under 35 U.S.C. 154(b) by 752 days.

(21) Appl. No.: 11/895,817

(22) Filed: Aug. 28, 2007
(Under 37 CFR 1.47)

(65) Prior Publication Data

US 2008/0073529 A1    Mar. 27, 2008

Related U.S. Application Data

(60) Provisional application No. 60/842,066, filed on Aug. 31, 2006.

(51) Int. Cl.
*H01J 49/00* (2006.01)
(52) U.S. Cl. ......................... 250/307; 250/310
(58) Field of Classification Search .................. 250/311, 250/310, 307
See application file for complete search history.

(56) References Cited

U.S. PATENT DOCUMENTS

| | | | | |
|---|---|---|---|---|
| 3,705,755 | A * | 12/1972 | Baer | 359/202.1 |
| 5,973,323 | A * | 10/1999 | Adler et al. | 250/310 |
| 6,548,810 | B2 * | 4/2003 | Zaluzec | 850/9 |
| 6,812,461 | B1 * | 11/2004 | Adler et al. | 850/9 |
| 6,885,000 | B1 * | 4/2005 | Adler | 850/1 |
| 6,960,773 | B2 * | 11/2005 | Menon et al. | 250/492.2 |
| 7,109,483 | B2 * | 9/2006 | Nakasuji et al. | 250/310 |
| 7,247,849 | B1 * | 7/2007 | Toth et al. | 250/307 |
| 7,462,829 | B2 * | 12/2008 | Nagahama et al. | 250/310 |
| 2002/0070340 | A1 * | 6/2002 | Veneklasen et al. | 250/310 |
| 2002/0104964 | A1 * | 8/2002 | Adler et al. | 250/307 |
| 2002/0130262 | A1 * | 9/2002 | Nakasuji et al. | 250/311 |
| 2003/0183763 | A1 * | 10/2003 | Bertsche | 250/310 |
| 2003/0205669 | A1 * | 11/2003 | Adler et al. | 250/310 |
| 2004/0069957 | A1 * | 4/2004 | Menon et al. | 250/492.2 |
| 2007/0045536 | A1 * | 3/2007 | Nakasuji et al. | 250/310 |
| 2008/0121804 | A1 * | 5/2008 | Nakasuji et al. | 250/310 |

OTHER PUBLICATIONS

International Search Report for Application No. PCT/US07/19188 (2 sheets), Filed Aug. 29, 2007.

* cited by examiner

*Primary Examiner* — Phillip A Johnston
*Assistant Examiner* — Johnnie Smith
(74) *Attorney, Agent, or Firm* — Okamoto & Benedicto LLP

(57) ABSTRACT

One embodiment relates to an apparatus using electrons for inspection or metrology of a semiconductor substrate. The apparatus includes an electron source, electron lenses, scan deflectors, an objective electron lens, a collection electron lens, a pin-hole filter, de-scan deflectors, and a detector. The collection electron lens is configured to focus the secondary electrons so as to form a secondary electron beam which is focused at a conjugate focal plane, and the pin-hole filter is positioned at the conjugate focal plane. The de-scan deflectors are configured to controllably deflect the secondary electrons so as to counteract an influence of the scan deflectors such that a center portion of the secondary electron beam passes through the filter and a remainder portion of the secondary electron beam is filtered out by the filter. Other embodiments and features are also disclosed.

20 Claims, 9 Drawing Sheets

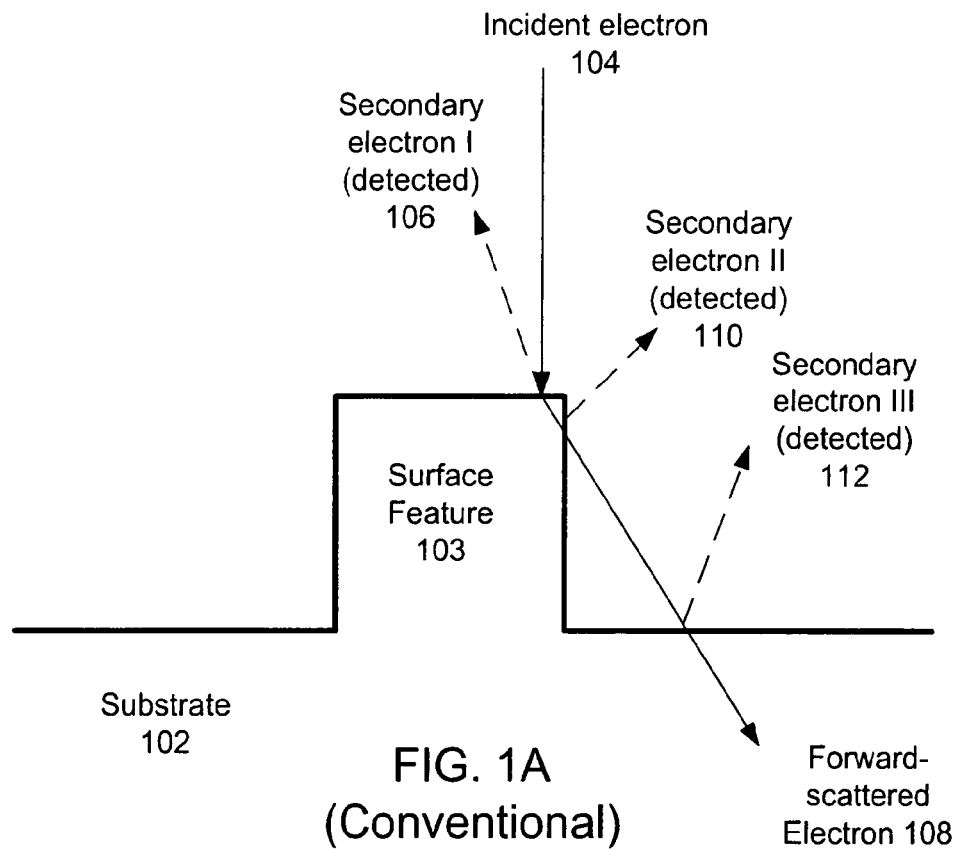
FIG. 1A (Conventional)
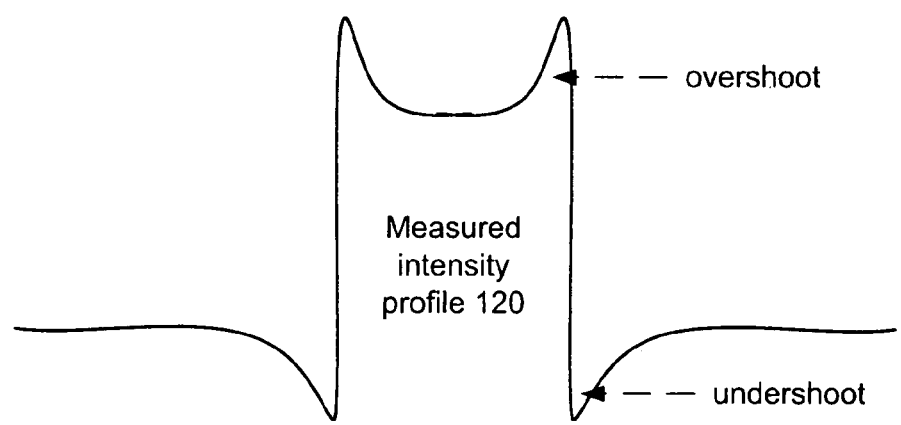
FIG. 1B (Conventional)

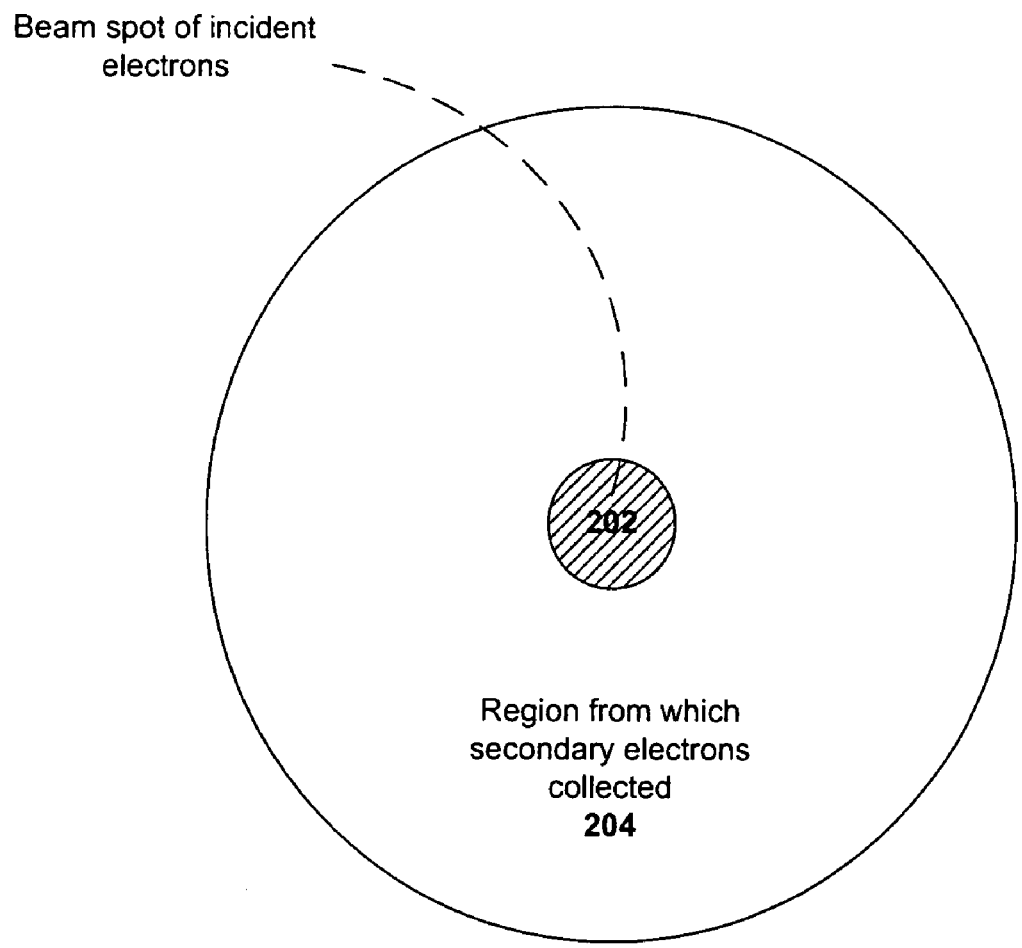
FIG. 2
(Conventional)

CONFOCAL SECONDARY ELECTRON IMAGING

CROSS-REFERENCE TO RELATED APPLICATION

The present application claims the benefit of U.S. Provisional Patent Application No. 60/842,066, entitled "Confocal Secondary Electron Imaging", filed Aug. 31, 2006, by inventor David L. Adler, the disclosure of which is hereby incorporated by reference in its entirety.

BACKGROUND OF THE INVENTION

1. Field of the Invention

The present invention relates generally to electron beam apparatus and methods of using same.

2. Description of the Background Art

Automated inspection and review systems are important in process control and yield management for the semiconductor and related microelectronics industries. Such systems include electron beam (e-beam) based systems and other types of systems.

BRIEF DESCRIPTION OF THE DRAWINGS

FIG. 1A is a schematic diagram of an example incident electron which is incident upon a surface feature of a substrate and causes a series of secondary electron emissions.

FIG. 1B shows an example of a typical measured intensity profile corresponding to the surface feature of FIG. 1A.

FIG. 2 is a diagram showing a beam spot and larger surrounding region from which secondary electrons are conventionally collected.

SUMMARY

Figure 3:
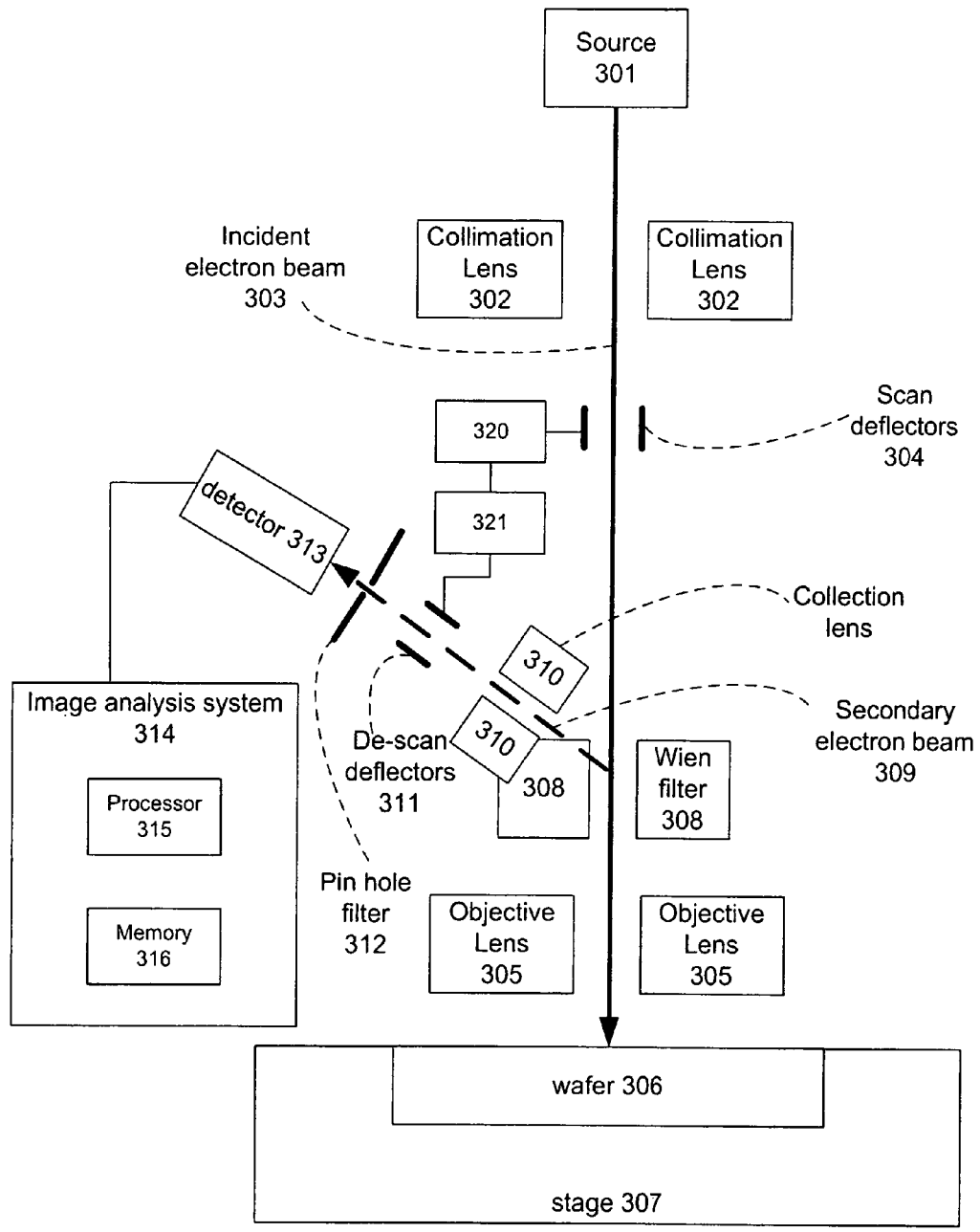
FIG. 3 is a schematic diagram of an apparatus for confocal secondary electron imaging in accordance with a first embodiment of the invention.

One embodiment pertains to a method of scanning electron beam imaging. Electrons are generated from an electron source, and an incident electron beam is formed from the generated electrons. The incident electron beam is controllably deflected in a time-dependent manner so as to cause scanning of a beam spot over an area of a substrate surface. The incident electron beam is focused onto the beam spot on the substrate surface, and the impingement of the incident electron beam onto the substrate surface causes secondary electrons to be emitted from a region surrounding and including the beam spot. The secondary electrons are focused by a collection electron lens so as to form a secondary electron beam which is focused at a conjugate focal plane. The secondary electrons are also controllably deflected so as to counteract an influence of said scanning such that a center portion of the secondary electron beam passes through a pin-hole filter positioned at the conjugate focal plane and a remainder portion of the secondary electron beam is filtered out by the filter. The portion of the secondary electron beam which passes through the pin-hole filter is detected.

An alternative embodiment relates to a method in which the secondary electron beam is detected using a two-dimensional position-sensitive array of detection elements so as to generate time-dependent two-dimensional detection data. The time-dependent two-dimensional detection data is processed so as to track time-dependent movement of the secondary electron beam and to apply a spatial filter which is centered on the time-dependent position of the secondary electron beam.

Another embodiment pertains to an apparatus using electrons for inspection or metrology of a semiconductor substrate. The apparatus includes an electron source, electron lenses, scan deflectors, an objective electron lens, a collection electron lens, a pin-hole filter, de-scan deflectors, and a detector. The electron source generates electrons, and the electron lenses form an incident electron beam from the generated electrons. The scan deflectors are configured to controllably deflect the incident electron beam in a time-dependent manner so as to cause scanning of a beam spot over an area of a substrate surface. The objective electron lens focuses the incident electron beam onto the beam spot on the substrate surface. Impingement of the incident electron beam onto the substrate surface causes secondary electrons to be emitted from a region surrounding and including the beam spot. The collection electron lens is configured to focus the secondary electrons so as to form a secondary electron beam which is focused at a conjugate focal plane. The pin-hole filter is positioned at the conjugate focal plane. The de-scan deflectors are configured to controllably deflect the secondary electrons so as to counteract an influence of said scanning such that a center portion of the secondary electron beam passes through the filter and a remainder portion of the secondary electron beam is filtered out by the filter. The detector detects the portion of the secondary electron beam which passes through the filter.

An alternative embodiment relates to an apparatus which includes a two-dimensional position-sensitive array of detection elements positioned at the conjugate focal plane and configured to detect the secondary electron beam so as to generate time-dependent two-dimensional detection data. The apparatus further includes an image analysis system configured to process the time-dependent two-dimensional detection data so as to track time-dependent movement of the secondary electron beam and to apply a spatial filter which is centered on the time-dependent position of the secondary electron beam.

Other embodiments and features are also disclosed.

DETAILED DESCRIPTION

FIG. 1A is a schematic diagram of an example incident electron 104 which is incident upon a surface feature 103 of a substrate 102 and causes a series of secondary electron emissions. The incident electron 104 impacts upon the surface feature 103 and so causes ejection of a first secondary electron (secondary electron I) 106 from the vicinity at or near the impact.

However, in this example, the emission of secondary electrons does not stop there. A forward-scattered electron 108 is also emitted. In this case, as the forward-scattered electron 108 exits the sidewall of the feature 103, a second secondary electron (secondary electron II) 110 is ejected from the sidewall. The forward-scattered electron 108 goes on to enter the substrate 102 and causes ejection of a third secondary electron (secondary electron III) 112 from the vicinity at or near the impact.

The example of FIG. 1A is just one of a multitude of scattering scenarios. As in the example of FIG. 1A, the ejection of secondary electrons is not limited to the vicinity at or near the initial impact of the incident electron. Instead, secondary electrons are emitted from a relatively large region surrounding the point of the initial incidence.

FIG. 1B shows an example of a typical measured intensity profile 120 corresponding to the surface feature of FIG. 1A. As seen, the measured intensity profile 120 overshoots and undershoots at the edges of the surface feature. The overshooting is caused from scattering scenarios similar to the example of FIG. 1A, where multiple secondary electrons are emitted and detected from a relatively large region.

FIG. 2 is a diagram showing a beam spot 202 and larger surrounding region 204 from which secondary electrons are conventionally collected. The beam spot 202 corresponds to the region of impact of incident electrons from the primary electron beam. The larger collection region 204 is due to scattering scenarios, such as that discussed in relation to FIG. 1A, where secondary electrons are ejected at a substantial distance away from the impact of an incident electron.

FIG. 3 is a schematic diagram of an apparatus 300 for confocal secondary electron imaging in accordance with a first embodiment of the invention. Such an apparatus may be used, for example, in automated inspection and review systems. The apparatus comprises, among other components, an electron gun or source 301, condenser or collimation lenses 302, scan deflectors 304, objective electron lens 305, Wien filter 308, collection electron lens 310, de-scan deflectors 311, a pin-hole filter 312, a detector 313, and an image analysis system 314.

The electron source 301 and the collimation lens 302 generate and form the incident electron beam 303. The scan deflectors 304 are configured to controllably deflect the incident beam 303 so that the beam spot is scanned over the area being imaged. The objective electron lens 305 focuses the incident electron beam 303 so that it impinges upon a surface of a semiconductor wafer (or other substrate) 306. As the incident beam 303 is scanned over the surface area, secondary electrons are emitted from the incident beam spot and from the surrounding region. The wafer 306 is shown as being held in a movable stage 307.

The Wien filter 308 is typically configured such that it does not deflect the incident electron beam 303 which is traveling in a direction towards the wafer 306, but it does deflect the secondary electron beam 309 which is traveling in a direction away from the wafer 306. In this example, the Wien filter 308 is configured to deflect the secondary electron beam towards the collection lens 310 of the detection system. In an alternate embodiment, another type of beam separator may be used instead of a Wien filter.

The collection lens 310 comprises an electron lens which is configured to focus the secondary electron beam 309 so as to form a conjugate focal plane. The pin-hole filter 312 is positioned at this conjugate focal plane.

De-scan deflectors 311 are configured to deflect the secondary electron beam 309 such that the distribution of secondary electrons is centered or nearly centered on the pin hole of the pin-hole filter 312. In other words, the de-scan deflectors 311 are configured to deflect the secondary electron beam 309 in a time-dependent way as to counteract the time-dependent deflection of the incident electron beam 303 by the scan deflectors 304.

The de-scan deflectors 311 may be implemented as electrostatic and/or electromagnetic deflectors. A de-scan controller 321 may be calibrated over a scan cycle so that the de-scanning effectively counteracts the scanning. The de-scan controller 321 may be communicatively coupled to the scan controller 320 so as to coordinate the timing of the scanning and de-scanning.

Because of the collection lens 310 and the de-scan deflectors 311, the pin-hole filter 312 is able to filter out secondary electrons emitted from locations on the wafer which are away from the incident beam spot. On the other hand, secondary electrons emitted from the region coincident or nearly coincident with the incident beam spot pass through the pin hole of the filter 312 and so are detected by the detector 313. In one implementation, the pin-hole filter 312 may comprise an aperture of fixed size. In another implementation, the pin-hole filter 312 may comprise an aperture with an adjustable size, such that the size of the hole (aperture) may be adjusted to enlarge or shrink the collection region.

An image analysis system 314 may be configured to retrieve, further process, and analyze image data obtained from the detector 313. The image analysis system 314 may comprise, for example, one or more processor 315 and memory 316 which is communicatively coupled to the processor 315, for example, by way of a bus communication system. The image analysis system 314 may also include a display (not shown), such as a monitor screen, and a user input (also not shown), such as a keyboard and mouse. The memory 316 may include various computer-readable and processor-executable code, such as, for example, to process the image data to detect defects in the wafer.

Figure 4:
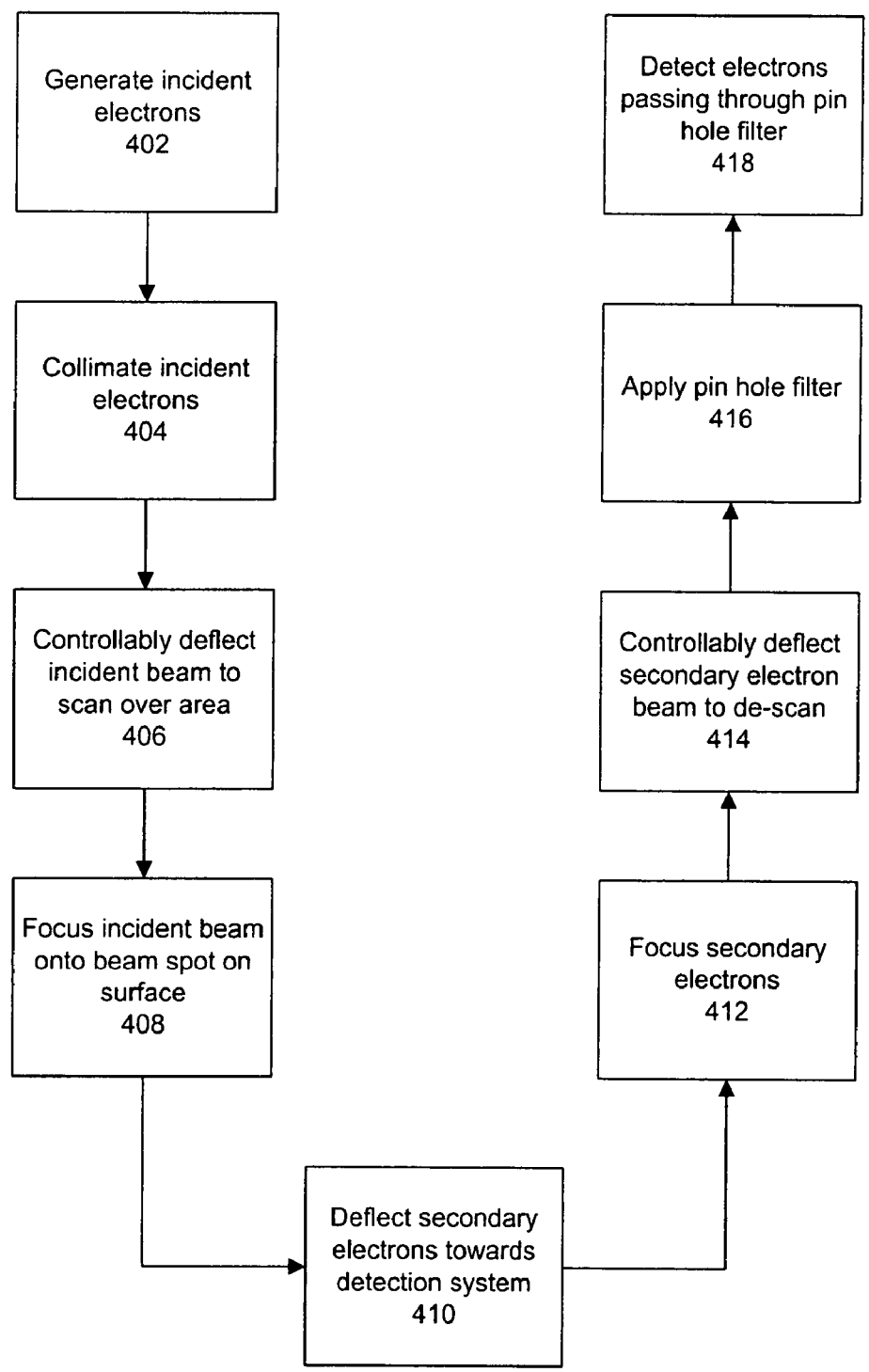
FIG. 4 is a flow chart of a method for confocal secondary electron imaging in accordance with a first embodiment of the invention.

FIG. 4 is a flow chart of a method 400 for confocal secondary electron imaging in accordance with a first embodiment of the invention. This method 400 may be implemented, for example, with the apparatus 300 described above in relation to FIG. 3.

Incident electrons are generated 402 by an electron source, and they are collimated 404 by condenser or collimation lenses to form an incident electron beam. The incident electron beam is controllably deflected 406 so that the beam is scanned over an area being imaged. The incident electron beam is focused 408 by an objective electron lens to form a focused beam spot upon a surface of the specimen (such as a semiconductor wafer). As the beam spot is scanned over the surface area, secondary electrons are emitted from the incident beam spot and from the region surrounding the incident beam spot.

The secondary electrons may then be deflected 410 towards the detection system. A Wien filter may be used for this purpose. The secondary electrons may then be focused 412 so as to form a secondary electron beam which is focused at a conjugate focal plane. This may be accomplished by a collection electron lens or lenses. In addition, the secondary electron beam may be controllably deflected 414 such that the secondary electron beam (i.e. the distribution of secondary electrons of the beam) is centered or nearly centered on the pin hole of the pin-hole filter. In other words, the de-scanning may be performed such that the secondary electron beam is deflected 414 in a time-dependent way so as to counteract the time-dependent deflection of the incident electron beam as it is scanned 406 over the specimen.

A pin-hole filter may then be applied 416 to filter out secondary electrons emitted from locations on the specimen which are away from the incident beam spot. On the other hand, secondary electrons emitted from the region coincident or nearly coincident with the incident beam spot pass through the pin-hole filter and so are detected 418.

Figure 5A:
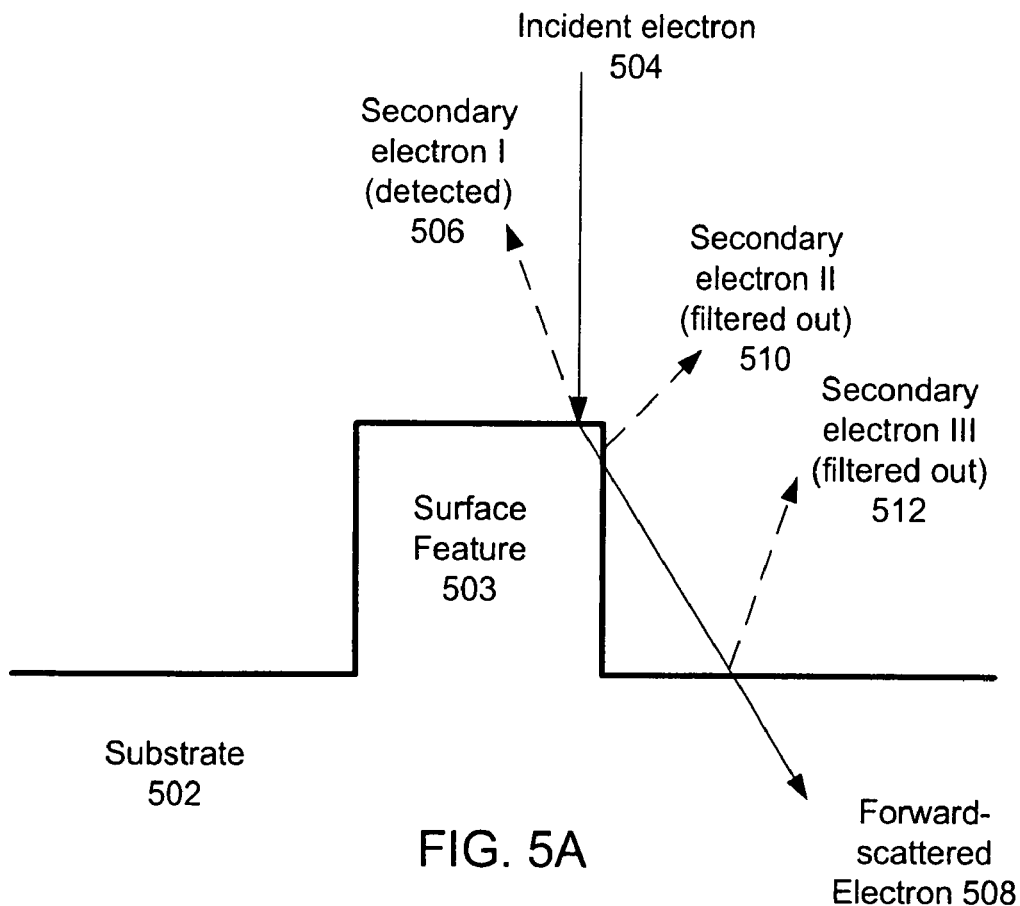
FIG. 5A is a schematic diagram an example incident electron which is incident upon a surface feature of a substrate and generates a series of secondary electron emissions, wherein the filtering out of certain electrons due to confocal secondary electron imaging is indicated in accordance with an embodiment of the invention.

FIG. 5A is a schematic diagram an example incident electron 504 which is incident upon a surface feature 503 of a substrate 502 and generates a series of secondary electron emissions. In contrast to the conventional electron imaging discussed in relation to FIG. 1A, the filtering out of certain electrons due to confocal secondary electron imaging is indicated in FIG. 5A in accordance with an embodiment of the invention.

The incident electron 504 impacts upon the surface feature 503 and so causes ejection of a first secondary electron (secondary electron I) 506 from the vicinity at or near the impact. In this case, because secondary electron I 506 is emitted from the area coincident with the incident beam spot, secondary electron I 506 passes through the pin-hole filter and is detected.

In this example, a forward-scattered electron 508 is also emitted. As the forward-scattered electron 508 exits the sidewall of the feature 503, a second secondary electron (secondary electron II) 510 is ejected from the sidewall. However, in this case, secondary electron II 510 is emitted from a point which is outside the area of the incident beam spot, such that secondary electron II 510 is filtered out by the pin-hole filter. Hence secondary electron II 510 is not detected and does not contribute to the detected intensity at that scan point.

The forward-scattered electron 508 goes on to enter the substrate 502 and causes ejection of a third secondary electron (secondary electron III) 512 from the vicinity at or near the impact. However, in this case, secondary electron III 512 is emitted from a point which is outside the area of the incident beam spot, such that secondary electron III 512 may be filtered out by the pin-hole filter. Hence, secondary electron III 512 is not detected and does not contribute to the measured intensity at that scan pixel.

The example of FIG. 5A is just one of a multitude of scattering scenarios. As in the example of FIG. 5A, the ejection of secondary electrons is not limited to the vicinity at or near the initial impact of the incident electron. Instead, secondary electrons are emitted from a relatively large region surrounding the point of the initial incidence.

Those secondary electrons emitted from points outside an area coincident or nearly coincident with the incident beam spot may be filtered out, such that they do not contribute to the measured intensity at that scan pixel. Those secondary electrons emitted from points inside an area coincident or nearly coincident with the incident beam spot may be pass through the filter, such that they do contribute to the measured intensity at that scan pixel.

Figure 5B:
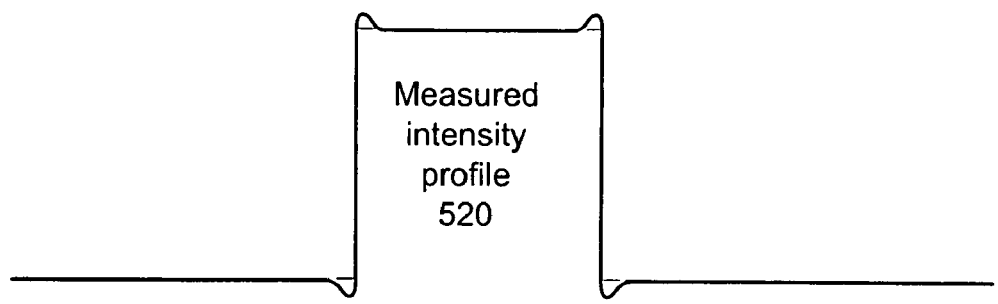
FIG. 5B shows an example of a measured intensity profile corresponding to the surface feature of FIG. 5A, wherein confocal secondary electron imaging is applied in accordance with an embodiment of the invention.

FIG. 5B shows an example of a measured intensity profile 520 corresponding to the surface feature of FIG. 5A, wherein confocal secondary electron imaging is applied in accordance with an embodiment of the invention. In comparison to the measured intensity profile 120 of FIG. 1B, the measured intensity profile 520 of FIG. 5B has reduced overshoot and undershoot at the edges of the surface feature. This reduction provides for more accurate imaging of the feature and is due to the intensities being measured by the confocal method and apparatus as disclosed in the present application.

Figure 6:
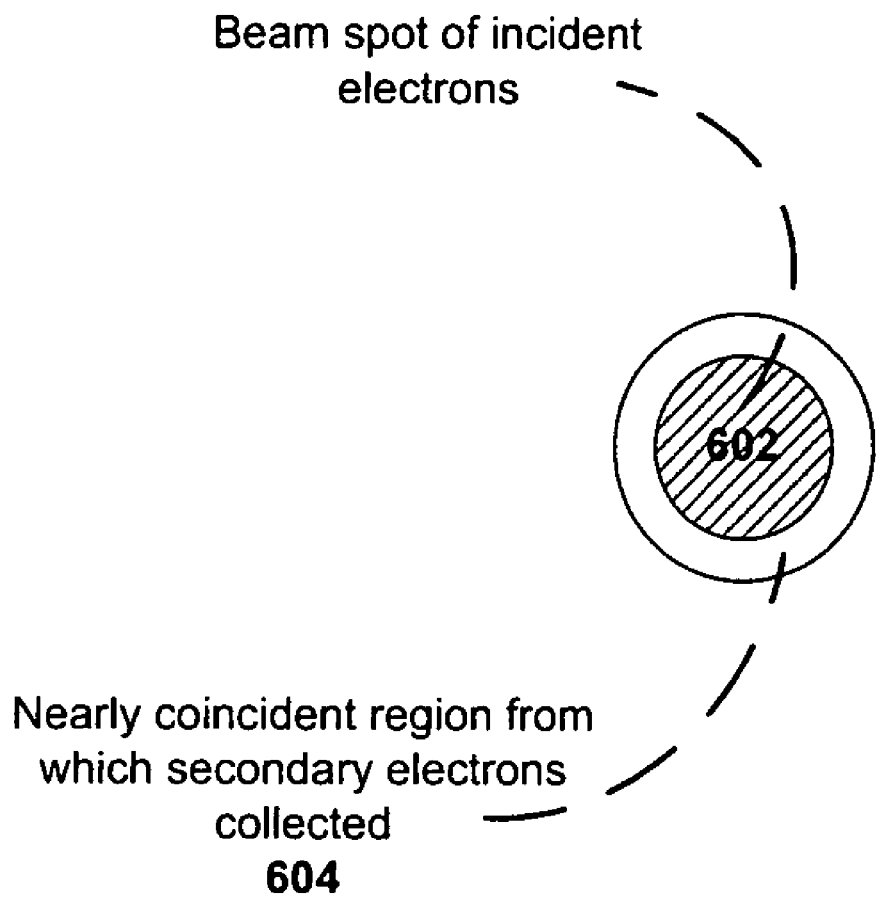
FIG. 6 is a diagram showing a beam spot and a nearly coincident surrounding region from which secondary electrons are collected when confocal secondary electron imaging is applied in accordance with an embodiment of the invention.

FIG. 6 is a diagram showing a beam spot and a nearly coincident surrounding region from which secondary electrons are collected when confocal secondary electron imaging is applied in accordance with an embodiment of the invention. The beam spot 602 corresponds to the region of impact of incident electrons from the primary electron beam. The nearly coincident collection region 604 from which secondary electrons are collected is due to the application of confocal secondary electron imaging as disclosed herein. For example, the area of the collection region 604 may be less than twice the area of the beam spot 602 so as to achieve nearly confocal electron imaging.

Although the collection region 604 shown in FIG. 6 is slightly larger than and surrounds the beam spot 602 for ease of illustration, the collection region 604 is preferably coincident with the beam spot 602 of incident electrons so as to achieve confocal electron imaging. Alternatively, the collection region 604 may be slightly smaller than and be within the beam spot 602 of incident electrons.

Figure 7:
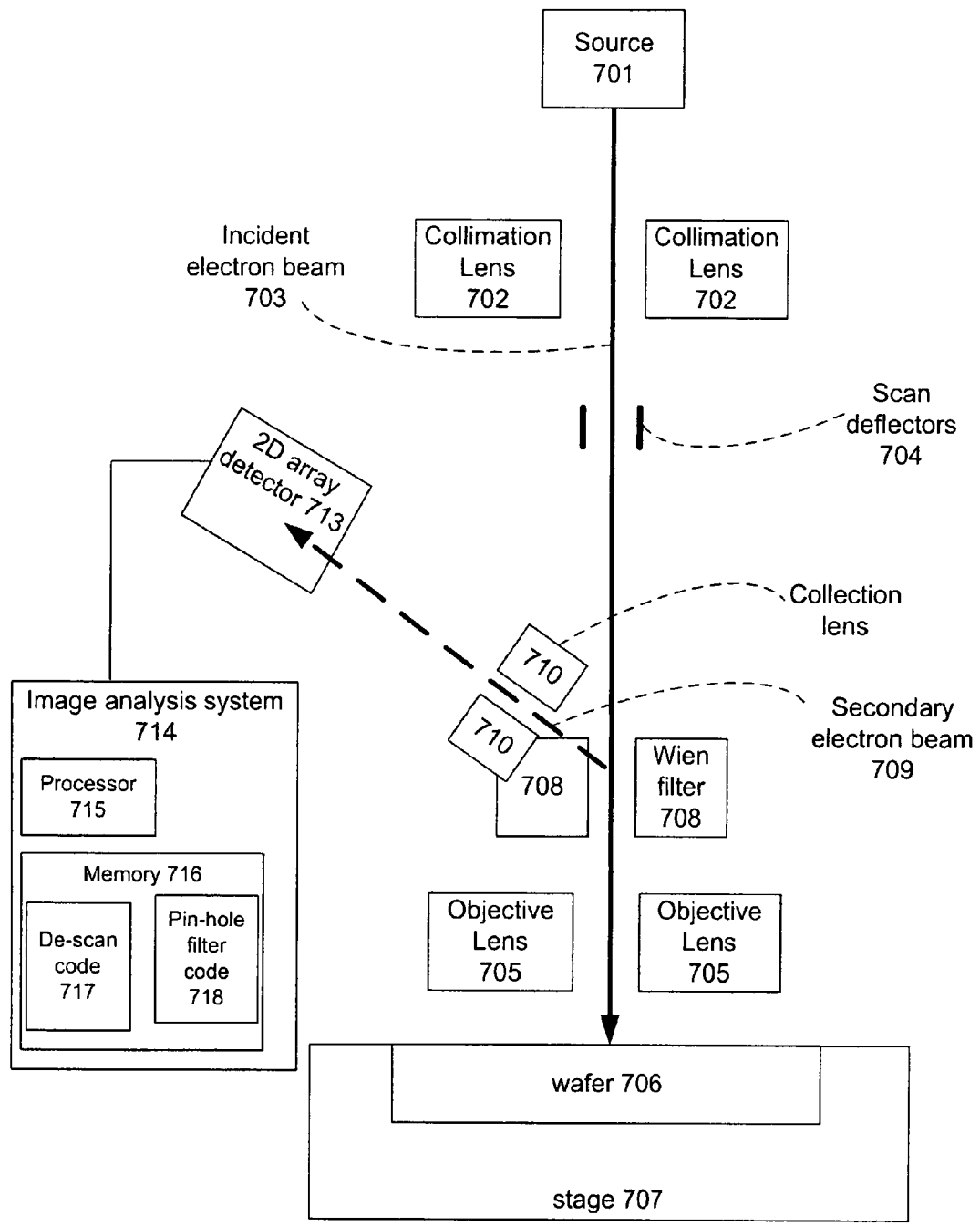
FIG. 7 is a schematic diagram of an apparatus for confocal secondary electron imaging in accordance with another embodiment of the invention.

FIG. 7 is a schematic diagram of an apparatus 700 for confocal secondary electron imaging in accordance with another embodiment of the invention. Such an apparatus may be used, for example, in automated inspection and review systems. The apparatus comprises, among other components, an electron gun or source 701, condenser or collimation lenses 702, scan deflectors 704, objective electron lens 705, Wien filter 708, collection electron lens 710, two-dimensional (2D) array detector 713, and an image analysis system 714.

The electron source 701 and the collimation lens 702 generate and form the incident electron beam 703. The scan deflectors 704 are configured to controllably deflect the incident beam 703 so that the beam spot is scanned over the area being imaged. The objective electron lens 705 focuses the incident electron beam 703 so that it impinges upon a surface of a semiconductor wafer (or other substrate) 706. As the incident beam 703 is scanned over the surface area, secondary electrons are emitted from the incident beam spot and from the surrounding region. The wafer 706 is shown as being held in a movable stage 707.

The Wien filter 708 is typically configured such that it does not deflect the incident electron beam 703 which is traveling in a direction towards the wafer 706, but it does deflect the secondary electron beam 709 which is traveling in a direction away from the wafer 706. In this example, the Wien filter 708 is configured to deflect the secondary electron beam towards the collection lens 710 of the detection system.

The collection lens 710 comprises an electron lens which is configured to focus the secondary electron beam 709 so as to form a conjugate focal plane. In this embodiment, the 2D array detector 713 is positioned at this conjugate focal plane.

The 2D array detector 713 detects secondary electrons in a position-sensitive manner. By being positioned in the conjugate focal plane, the position-distribution of detected secondary electrons has a correspondence to emission locations from the specimen.

The image analysis system 714 may be configured to retrieve, further process, and analyze image data obtained from the detector 713. The image analysis system 714 may comprise, for example, one or more processor 715 and memory 716 which is communicatively coupled to the processor 715, for example, by way of a bus communication system. The image analysis system 714 may also include a display (not shown), such as a monitor screen, and a user input (also not shown), such as a keyboard and mouse. The memory 716 may include various computer-readable and processor-executable code, such as, for example, to process the image data to detect defects in the wafer. In accordance with this embodiment, the memory 716 includes computer-readable and processor-executable de-scan code 717 and pin-hole filter code 718.

The de-scan code 717 is configured to follow and track a detected center of the secondary electron beam. In other words, the de-scan code 717 is configured to track the secondary electron beam in a time-dependent way as to be able to account for the time-dependent deflection of the incident electron beam 703 by the scan deflectors 704.

The pin-hole filter code 718 is configured to filter out those secondary electrons detected at positions away from the center of the secondary electron beam. On the other hand, secondary electrons near the center of the secondary electron beam are not filtered out by the pin-filter code 718.

In effect, the de-scan code 717 and pin-hole filter code 718 are configured to perform the de-scanning and filtering functions via computer processing.

Figure 8:
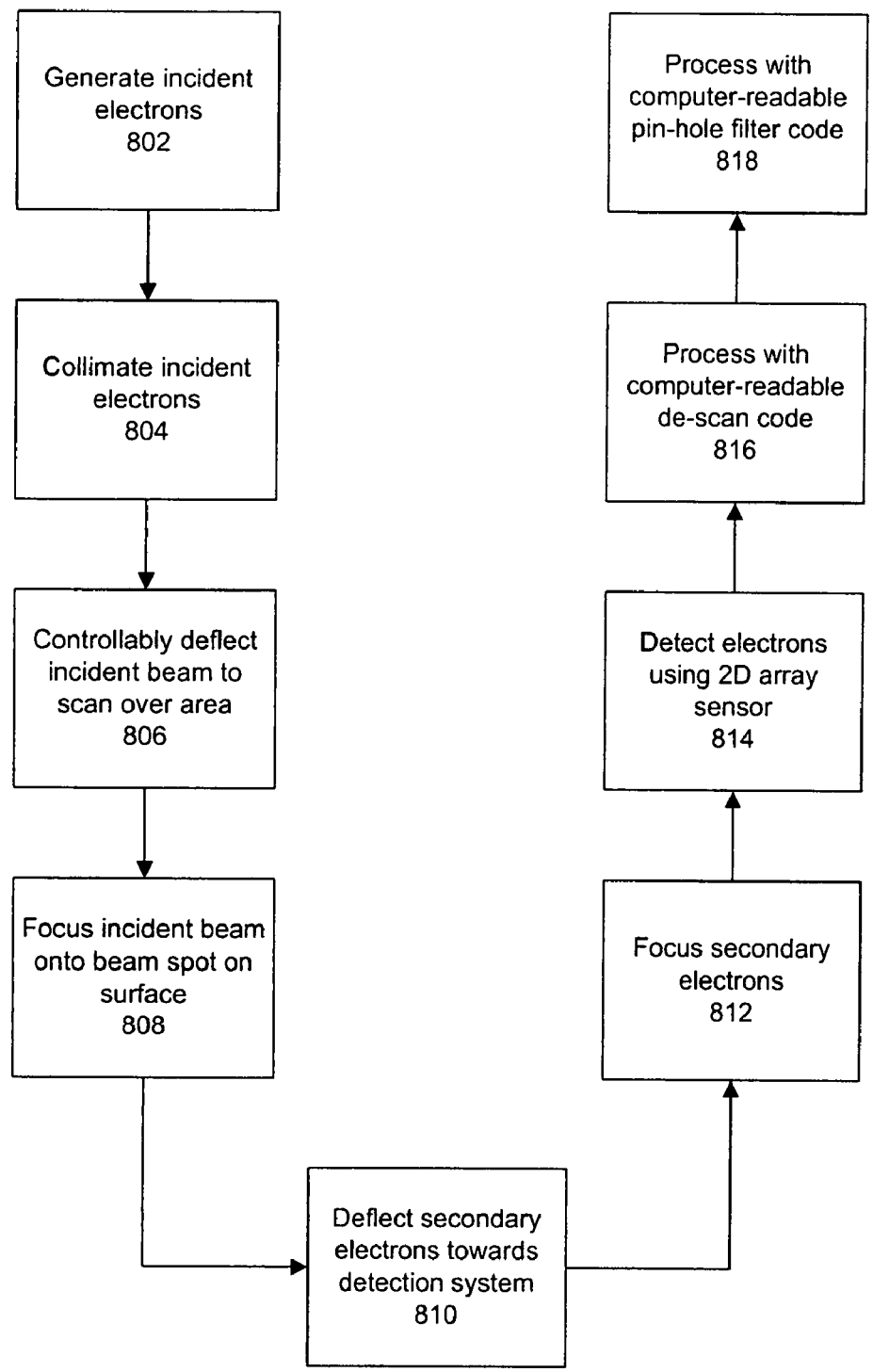
FIG. 8 is a flow chart of a method for confocal secondary electron imaging in accordance with another embodiment of the invention.

FIG. 8 is a flow chart of a method 800 for confocal secondary electron imaging in accordance with another embodiment of the invention. This method 800 may be implemented, for example, with the apparatus 700 described above in relation to FIG. 7.

Incident electrons are generated 802 by an electron source, and they are collimated 804 by condenser or collimation lenses to form an incident electron beam. The incident electron beam is controllably deflected 806 so that the beam is scanned over an area being imaged. The incident electron beam is focused 808 by an objective electron lens to form a focused beam spot upon a surface of the specimen (such as a semiconductor wafer). As the beam spot is scanned over the surface area, secondary electrons are emitted from the incident beam spot and from the region surrounding the incident beam spot.

The secondary electrons may then be deflected 810 towards the detection system. A Wien filter may be used for this purpose. The secondary electrons may then be focused 812 so as to form a conjugate focal plane. This may be accomplished by a collection electron lens or lenses.

Secondary electrons are detected 814 in a position-sensitive manner using a 2D array sensor. By having the 2D array sensor positioned in the conjugate focal plane, the position-distribution of detected secondary electrons has a correspondence to emission locations from the specimen.

The image data obtained from the 2D detector may then be processed and analyzed. In particular, the image data may be processed 816 by computer-readable and processor-executable de-scan code so as to track a center of the secondary electron beam. In other words, the de-scan code may track the secondary electron beam in a time-dependent way as to be able to account for the time-dependent deflection of the incident electron beam by the scan deflectors.

The image data may also be processed 818 by computer-readable and processor-executable pin-hole filter code so as to filter out those secondary electrons detected at positions away from the center of the secondary electron beam. On the other hand, secondary electrons near the center of the secondary electron beam are not filtered out by the pin-filter code.

In effect, the processing (816 and 818) by the de-scan code and the pin-hole filter code perform the de-scanning and filtering functions via computer processing.

The above discussion describes the use of pin-hole filter code which functions as a step function to either filter out or not detected electron data based on the detected position relative to a center. In an alternate embodiment, the pin-hole filter code may employ a filter which is not a step function. For example, the filter may be a Gaussian probability distribution function or other probability distribution function to either filter out or not detected electron data based on the detected position relative to a center.

Lower beam energies are desirable for reduced damage to wafers and other specimens and for better resolution due to the smaller detected interaction volume. However, lower beam energies also typically result in reduced depth of field as discussed in the following.

According to theory, the depth of field of electron imaging which is achievable is proportional to the wavelength divided by the square of the numerical aperture of the beam. However, for a constant beam spot size, the numerical aperture is proportional to the wavelength. In other words, for a constant beam spot size, as the wavelength of the incident electrons becomes longer (i.e. the beam energy becomes lower), the numerical aperture becomes proportional larger. Since the depth of field is proportional to the wavelength divided by the square of the numerical aperture, the depth of field is reduced as the beam energy becomes lower (given a constant spot size).

An embodiment of the present invention may be applied to achieve better resolution due to the smaller detected interaction volume from confocal imaging, without the need to lower beam energies. Hence, the confocal imaging advantageously provides for high resolution while avoiding a corresponding reduction in the depth of field. Therefore, the confocal imaging according to the present disclosure may be applied to successfully image depth slices at high resolution.

Figure 9:
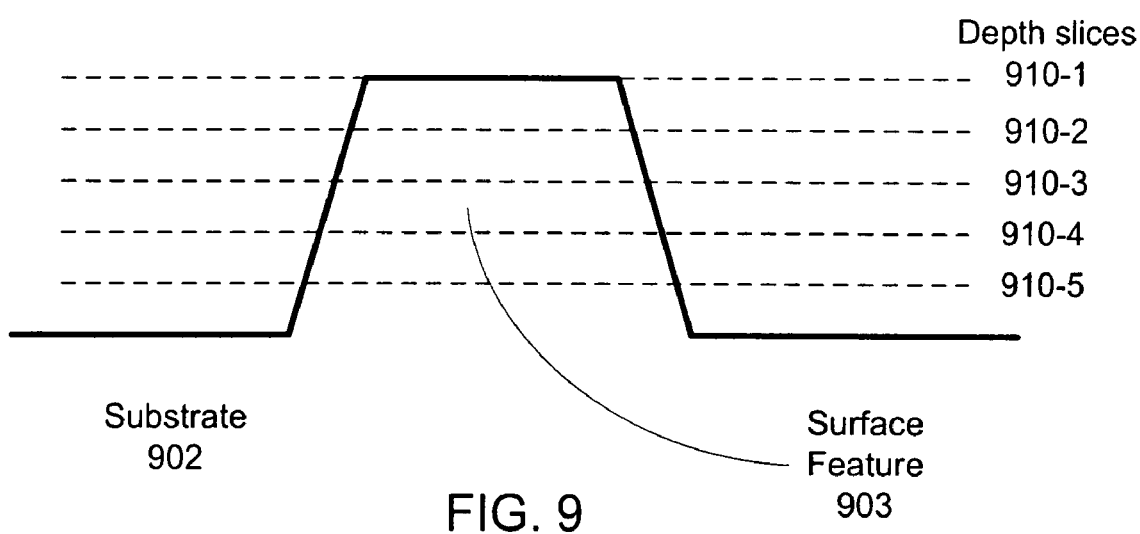
FIG. 9 is a schematic diagram depicting depth slices which may be imaged in accordance with an embodiment of the invention.

FIG. 9 is a schematic diagram depicting depth slices 910 which may be imaged in accordance with an embodiment of the invention. The diagram shows a profile of a substrate 902 and a surface feature 903 on the substrate. Multiple depth slices 910 are indicated at varying depths with respect to the feature 903.

The above-described diagrams are not necessarily to scale and are intended be illustrative and not limiting to a particular implementation. The above-described invention may be used, for example, in an automatic inspection or review system and applied to the inspection or review of wafers, optical masks, X-ray masks, electron-beam-proximity masks and stencil masks and similar substrates in a production environment.

In the above description, numerous specific details are given to provide a thorough understanding of embodiments of the invention. However, the above description of illustrated embodiments of the invention is not intended to be exhaustive or to limit the invention to the precise forms disclosed. One skilled in the relevant art will recognize that the invention can be practiced without one or more of the specific details, or with other methods, components, etc. In other instances, well-known structures or operations are not shown or described in detail to avoid obscuring aspects of the invention. While specific embodiments of, and examples for, the invention are described herein for illustrative purposes, various equivalent modifications are possible within the scope of the invention, as those skilled in the relevant art will recognize.

These modifications can be made to the invention in light of the above detailed description. The terms used in the following claims should not be construed to limit the invention to the specific embodiments disclosed in the specification and the claims. Rather, the scope of the invention is to be determined by the following claims, which are to be construed in accordance with established doctrines of claim interpretation.

What is claimed is:

1. A method of scanning electron beam imaging, the method comprising:
generating electrons from an electron source;
forming an incident electron beam from the generated electrons;
controllably deflecting the incident electron beam in a time-dependent manner so as to cause scanning of a beam spot over an area of a substrate surface;
focusing the incident electron beam onto the beam spot on the substrate surface, wherein impingement of the incident electron beam onto the substrate surface causes secondary electrons to be emitted from a region surrounding and including the beam spot;
focusing the secondary electrons by a collection electron lens so as to form a secondary electron beam which is focused at a conjugate focal plane;
controllably deflecting the secondary electrons so as to counteract an influence of said scanning such that a center portion of the secondary electron beam passes through a pin-hole filter positioned at the conjugate focal plane and a remainder portion of the secondary electron beam is filtered out by the filter; and
detecting the portion of the secondary electron beam which passes through the pin-hole filter.

2. The method of claim 1, wherein the center portion of the secondary electron beam which passes through the filter corresponds to secondary electrons emitted from a collection region of the substrate surface which is coincident with the beam spot and which moves with the beam spot as the beam spot is scanned.

3. The method of claim 2, wherein the remainder portion of the secondary electron beam which is filtered out by the filter corresponds to secondary electrons emitted from outside the beam spot.

4. The method of claim 1, wherein the center portion of the secondary electron beam which passes through the filter corresponds to secondary electrons emitted from a collection region of the substrate surface which smaller than and within the beam spot and which moves with the beam spot as the beam spot is scanned.

5. The method of claim 1, wherein the center portion of the secondary electron beam which passes through the filter corresponds to secondary electrons emitted from a collection region of the substrate surface which encompasses the beam spot and which moves with the beam spot as the beam spot is scanned, wherein the collection region has an area less than twice an area of the beam spot.

6. The method of claim 1, wherein said deflection of the incident electron beam is controlled by a scan controller, wherein said deflection of the secondary electrons is controlled by a de-scan controller, and wherein the scan and de-scan controllers are communicatively coupled so as to coordinate timing of said deflections.

7. The method of claim 1, further comprising deflecting the secondary electrons by a beam separator prior to said focusing by the collection electron lens.

8. An apparatus using electrons for inspection or metrology of a semiconductor substrate, the apparatus comprising:
an electron source for generating electrons;
electron lenses configured to form an incident electron beam from the generated electrons;
scan deflectors configured to controllably deflect the incident electron beam in a time-dependent manner so as to cause scanning of a beam spot over an area of a substrate surface;
an objective electron lens configured to focus the incident electron beam onto the beam spot on the substrate surface, wherein impingement of the incident electron beam onto the substrate surface causes secondary electrons to be emitted from a region surrounding and including the beam spot;
a collection electron lens configured to focus the secondary electrons so as to form a secondary electron beam which is focused at a conjugate focal plane;
a pin-hole filter positioned at the conjugate focal plane;
de-scan deflectors configured to controllably deflect the secondary electrons so as to counteract an influence of said scanning such that a center portion of the secondary electron beam passes through the filter and a remainder portion of the secondary electron beam is filtered out by the filter; and
a detector configured to detect the portion of the secondary electron beam which passes through the filter.

9. The apparatus of claim 8, wherein the center portion of the secondary electron beam which passes through the filter corresponds to secondary electrons emitted from a collection region of the substrate surface which is coincident with the beam spot and which moves with the beam spot as the beam spot is scanned.

10. The apparatus of claim 8, wherein the center portion of the secondary electron beam which passes through the filter corresponds to secondary electrons emitted from a collection region of the substrate surface which smaller than and within the beam spot and which moves with the beam spot as the beam spot is scanned.

11. The apparatus of claim 8, wherein the center portion of the secondary electron beam which passes through the filter corresponds to secondary electrons emitted from a collection region of the substrate surface which encompasses the beam spot and which moves with the beam spot as the beam spot is scanned, wherein the collection region has an area less than twice an area of the beam spot.

12. The apparatus of claim 8, wherein the pin-hole filter comprises an aperture with an adjustable size.

13. The apparatus of claim 8, wherein the pin-hole filter comprises an aperture with a fixed size.

14. The apparatus of claim 8, further comprising:
a scan controller configured to control said deflection of the incident electron beam by the scan deflectors; and
a de-scan controller configured to control said deflection of the secondary electrons by the de-scan deflectors,
wherein the scan and de-scan controllers are communicatively coupled so as to coordinate timing of said deflections.

15. The apparatus of claim 8, further comprising
a beam separator configured to deflect the secondary electrons prior to said focusing by the collection electron lens.

16. A method of scanning electron beam imaging, the method comprising:
generating electrons from an electron source;
forming an incident electron beam from the generated electrons;
controllably deflecting the incident electron beam in a time-dependent manner so as to cause scanning of a beam spot over an area of a substrate surface;
focusing the incident electron beam onto the beam spot on the substrate surface, wherein impingement of the incident electron beam onto the substrate surface causes secondary electrons to be emitted from a region surrounding and including the beam spot;

focusing the secondary electrons by a collection electron lens so as to form a secondary electron beam which is focused at a conjugate focal plane;

detecting the secondary electron beam using a two-dimensional position-sensitive array of detection elements so as to generate time-dependent two-dimensional detection data; and processing the time-dependent two-dimensional detection data so as to track time-dependent movement of the secondary electron beam and to apply a spatial filter which is centered on the time-dependent position of the secondary electron beam.

17. The method of claim 16, wherein the spatial filter comprises a pin-hole filter which filters out those secondary electrons detected at positions away from a center of the secondary electron beam.

18. The method of claim 16, wherein said deflection of the incident electron beam is controlled by a scan controller, wherein said deflection of the secondary electrons is controlled by a de-scan controller, and wherein the scan and de-scan controllers are communicatively coupled so as to coordinate timing of said deflections.

19. An apparatus using electrons for inspection or metrology of a semiconductor substrate, the apparatus comprising:

an electron source for generating electrons;

electron lenses configured to form an incident electron beam from the generated electrons;

scan deflectors configured to controllably deflect the incident electron beam in a time-dependent manner so as to cause scanning of a beam spot over an area of a substrate surface;

an objective electron lens configured to focus the incident electron beam onto the beam spot on the substrate surface, wherein impingement of the incident electron beam onto the substrate surface causes secondary electrons to be emitted from a region surrounding and including the beam spot;

a collection electron lens configured to focus the secondary electrons so as to form a secondary electron beam which is focused at a conjugate focal plane;

a two-dimensional position-sensitive array of detection elements positioned at the conjugate focal plane and configured to detect the secondary electron beam so as to generate time-dependent two-dimensional detection data; and an image analysis system configured to process the time-dependent two-dimensional detection data so as to track time-dependent movement of the secondary electron beam and to apply a spatial filter which is centered on the time-dependent position of the secondary electron beam.

20. The apparatus of claim 19, wherein the spatial filter comprises a pin-hole filter which filters out those secondary electrons detected at positions away from a center of the secondary electron beam.

* * * * *